(12) United States Patent
Huxel et al.

(10) Patent No.: US 7,645,282 B2
(45) Date of Patent: Jan. 12, 2010

(54) METHOD AND DEVICE FOR CUTTING SURGICAL WIRE OR CABLE

(75) Inventors: Shawn T. Huxel, Lawrenceville, NJ (US); Oliver Buchert, Wallington, NJ (US)

(73) Assignee: Osseus, LLC, Oviedo, FL (US)

( * ) Notice: Subject to any disclaimer, the term of this patent is extended or adjusted under 35 U.S.C. 154(b) by 312 days.

(21) Appl. No.: 10/992,799

(22) Filed: Nov. 19, 2004

(65) Prior Publication Data

US 2005/0149086 A1 Jul. 7, 2005

Related U.S. Application Data

(60) Provisional application No. 60/523,850, filed on Nov. 20, 2003.

(51) Int. Cl.
*A61B 17/58* (2006.01)
*A61B 17/60* (2006.01)
*A61F 2/00* (2006.01)

(52) U.S. Cl. .......................... 606/103; 606/60; 606/86 R (58) Field of Classification Search ................. 606/103, 606/53, 79, 144–145, 148, 220–232, 151, 606/116, 72, 74–75
See application file for complete search history.

(56) References Cited

U.S. PATENT DOCUMENTS

| | | | |
|---|---|---|---|
| 2,485,531 A | 10/1949 | Dzus et al. | |
| 2,708,437 A * | 5/1955 | Hutchins | 600/104 |
| 3,513,848 A | 5/1970 | Winston et al. | |
| 3,931,667 A | 1/1976 | Merser et al. | |
| 4,535,764 A | 8/1985 | Ebert | |
| 4,653,309 A | 3/1987 | Hendricks et al. | |
| 4,688,561 A | 8/1987 | Reese | |
| 4,738,255 A | 4/1988 | Goble | |
| 4,741,330 A | 5/1988 | Hayhurst | |
| 4,796,612 A | 1/1989 | Reese | |
| 4,889,110 A | 12/1989 | Galline et al. | |
| 5,041,129 A | 8/1991 | Hayhurst et al. | |
| 5,098,433 A | 3/1992 | Freedland | |
| 5,102,421 A | 4/1992 | Anspach, Jr. | |
| 5,108,433 A | 4/1992 | May et al. | |
| 5,116,340 A | 5/1992 | Songer et al. | |
| 5,230,129 A | 7/1993 | Scruggs | |
| 5,250,049 A | 10/1993 | Michael | |
| 5,269,797 A * | 12/1993 | Bonati et al. | 606/170 |
| 5,306,301 A | 4/1994 | Graf et al. | |
| 5,312,410 A | 5/1994 | Miller et al. | |
| 5,318,566 A | 6/1994 | Miller | |
| 5,395,374 A | 3/1995 | Miller et al. | |
| 5,405,359 A | 4/1995 | Pierce | |
| 5,417,700 A | 5/1995 | Egan | |
| 5,449,361 A | 9/1995 | Preissman | |
| 5,505,733 A | 4/1996 | Justin et al. | |

(Continued)

*Primary Examiner*—(Jackie) Tan-Uyen T Ho
*Assistant Examiner*—Melanie Tyson
(74) *Attorney, Agent, or Firm*—Haynes and Boone LLP (57) ABSTRACT

A method and device for cutting orthopedic cable including tensioning and crimping the cable in a desired position within a surgical cavity. A free end of the cable is inserted a device with two coaxial members having coordinating shearing faces. The shearing faces are moved along the cable to a position proximate a portion of the cable to be cut. Cutting is achieved is by rotating the coaxial members with respect to one another.

13 Claims, 7 Drawing Sheets

U.S. PATENT DOCUMENTS

| | | |
|---|---|---|
| 5,505,735 A | 4/1996 | Li |
| 5,536,270 A | 7/1996 | Songer et al. |
| 5,601,557 A | 2/1997 | Hayhurst |
| 5,643,289 A | 7/1997 | Sauer et al. |
| 5,645,588 A | 7/1997 | Graf et al. |
| 5,772,663 A | 6/1998 | Whiteside et al. |
| 5,879,357 A * | 3/1999 | Heaton et al. ............... 606/116 |
| 6,019,762 A | 2/2000 | Cole |
| 6,068,648 A * | 5/2000 | Cole et al. .................. 606/232 |
| 6,544,267 B1 | 4/2003 | Cole et al. |

* cited by examiner

METHOD AND DEVICE FOR CUTTING SURGICAL WIRE OR CABLE

CROSS REFERENCE

This application claims the benefit of U.S. Provisional Patent Application Ser. No. 60/523,850 filed Nov. 20, 2003, which is hereby incorporated by reference in its entirety.

BACKGROUND

The present invention relates to surgical devices and methods and, more particularly, to devices and methods for cutting surgical wire and cable.

It is a common requirement in orthopedic surgical procedures to anchor two or more elements together, such as pieces of a bone, two or more bones, or a combination of soft tissue and bone. This has been accomplished by a number of devices, such as bone bolts that penetrate two pieces of bone and use a nut to draw the segments together, bone screws and interconnecting plates, wires circling at least two pieces of bone, or sutures into the tissue. Often such devices require a relatively large access opening through surrounding and/or covering tissue to implant the anchoring devices. The enlarged access site may increase patient pain and lengthen recovery time. Further, in some locations it is difficult and impractical to make large access points to reach the appropriate site because of surrounding joints and vessels. Even with devices that penetrate the tissue in a substantially linear manner, i.e. lag bolts, the fracture must often be reduced before drilling and insertion of the bolt. Further, some of these devices may be difficult to use since it may be hard to reduce a fracture between two bone segments and maintain that reduction while the device is inserted. This is particularly true with small bone fragments were the use of threaded implants may tend to rotate one bone segment with respect to another, thereby creating a misalignment between the fragments.

One approach to solving this problem is the use of cerclage systems that provide an alternative to implants that must penetrate the bone to achieve fixation. These systems rely on passing a cable around two segments of bone and then tensioning the cable to squeeze the bone segments together.

Another approach to solving the problem of cable fixation is to provide a system of implants and instruments that allow an implant mounted on a flexible tension member to track through a hole drilled across the fracture, providing reduction and fixation of the fracture. The tension member may be implanted through bones as opposed to around them, as in a cerclage system. It may also be possible to use a monofilament wire, rather than a cable as the flexible tension member in the fixation system. In either event, there remains a need for a convenient and effective system for securing two segments of tissue together.

SUMMARY

A method of cutting surgical tension member is disclosed. The method includes tensioning and affixing a locking element on the surgical tension member in a desired position within a surgical cavity, inserting a free end of the surgical tension member into a device with two coaxial members having coordinating shearing faces, moving the shearing faces along the cable to a position proximate a portion of the cable to be cut, and rotating the coaxial members with respect to one another. Another method of a cutting surgical tension member is disclosed. The method includes setting a fractured bone in a desired position utilizing a length of orthopedic wire or cable, and tensioning and crimping the cable or wire next to the bone utilizing a first surgical opening. The method further includes inserting a proximal end of the cable or wire into first and second tubular coaxial members having coordinating, off-center openings on a distal end, moving the distal end of the first and second coaxial members along the cable or wire and into the first surgical cavity to position proximate the crimping, rotating the coaxial members with respect to one another to exert a shear cutting force on the surgical wire or cable, and removing the severed length of cable and the coaxial members from the first surgical opening.

A device for cutting a surgical tension member is disclosed. The device includes, first and second coaxial members each having an opening in a distal end and an actuatable handle adapted to retain and engage the first and second coaxial members and at a proximal end and to rotate the first coaxial member relative to the second. The openings in the distal ends of the coaxial members function as coordinating shearing faces when the handle is actuated. Another device for cutting a surgical tension member is disclosed. The device includes first and second gripping members pivotally attached to one another, first and second handle grips formed on proximal ends of the first and second gripping members, respectively, an outer tubular member attached on a proximal end to a distal end of the first gripping member substantially orthogonal to the first gripping member, an inner tubular member within the outer tubular member and having at least one pin radially attached on a circumference of a proximal end, and a movable barrel interposing the first and second tubular members along a length of a portion of the proximal ends of each and having at least one helical groove configured to engage the at least one pin of the inner tubular member. A distal end of the second gripping member is attached to a proximal end of the movable barrel and the distal ends of the outer tubular member and inner tubular member have openings that are off-center but substantially aligned such as allow a surgical cable or wire to pass through and to exert a shearing force on the cable or wire when the inner tubular member rotates with respect to the outer tubular member as a result of drawing together the first and second handle grips, the correspondent movement of the moveable barrel, and the interaction of the at least one helical groove with the at least one pin.

A surgical device for translating grip force to cutting force is disclosed. The device includes an inner cylinder disposed coaxially within an outer cylinder, a movable barrel interposing the inner and outer cylinders along a portion of a length of the cylinders and proximate a first end of the cylinders, and a squeezable grip secured to the outer cylinder and adapted to actuate the movable barrel lengthwise between the cylinders when the grip is squeezed. The movable barrel has one or more helical tracks configured to interact with one or more pins attached to the inner cylinder.

The foregoing has outlined features of several embodiments so that those skilled in the art may better understand the detailed description that follows. Additional features will be described below that may further form the subject of the claims herein. Those skilled in the art should appreciate that they can readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Figure 1:
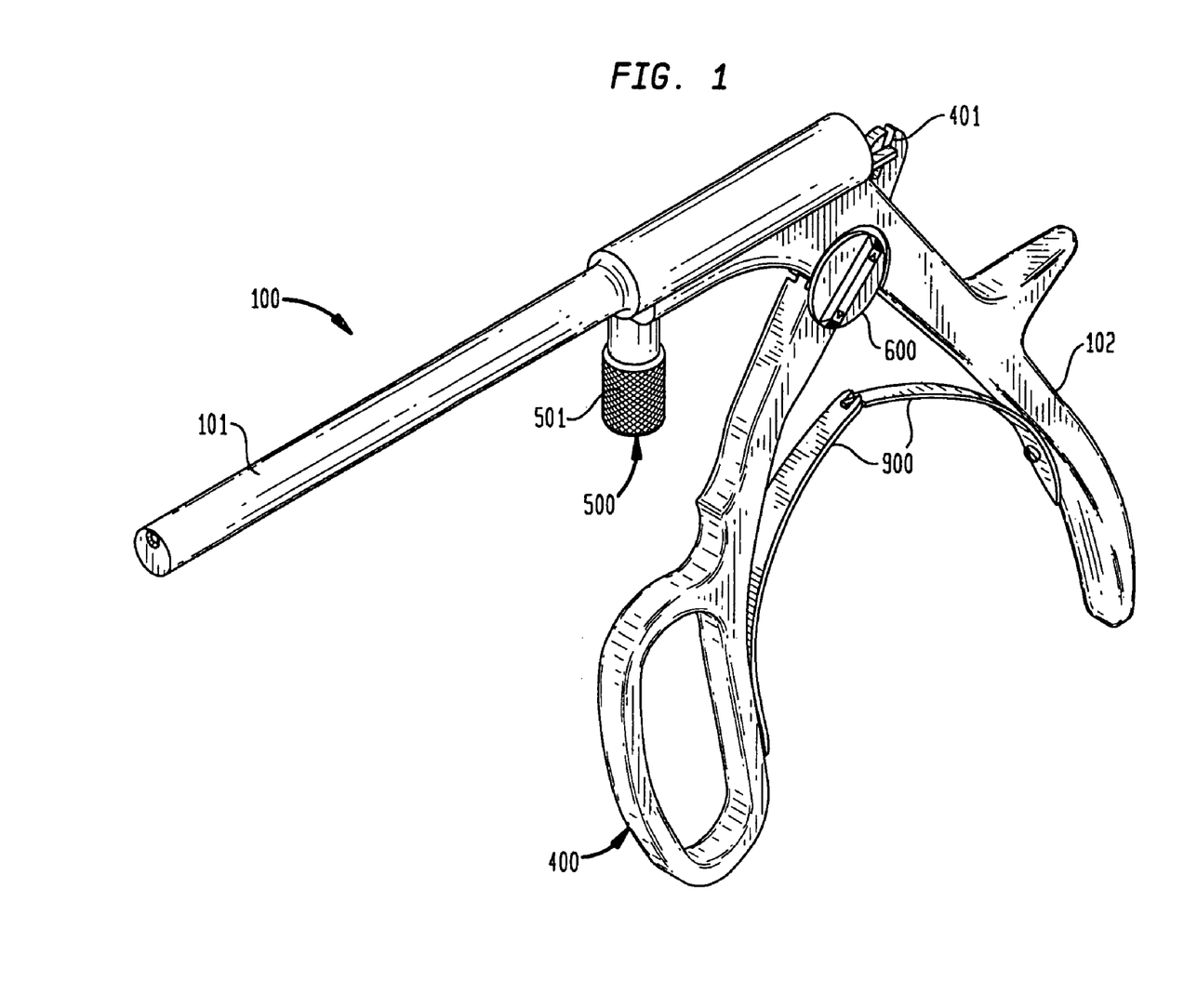
FIG. 1 is a perspective view of one embodiment of a device for cutting a surgical tension member.

Referring to FIG. 1, a perspective view of one embodiment of a device 100 for cutting surgical wire or cable is shown. A movable handle 400 with a slot 401 and a stationary handle 102 are pivotally connected by a lock 600. An outer nose 101 is provided along with a nose retaining element 500 with knurled surface 501. A spring 900 provides an opening bias between the movable handle 400 and the stationary handle 102.

The stationary handle 102 may be made from surgical grade stainless steel, plastic, polymers, or other suitable materials or combinations thereof. The stationary handle 102 may be formed by casting, machining, polishing, and/or other methods or combinations thereof. The exact dimensions of the stationary handle 102 may vary with the application, but the size will generally be such that an operator may maintain a comfortable and effective grip on the device 100 during operation, which is described in greater detail below.

The movable handle 400 may be made from similar or different materials than the stationary handle 102, including surgical grade stainless steel, plastic, polymers, or other suitable materials or combinations thereof. The movable handle 400 may be formed by casting, machining, polishing, and/or other methods or combinations thereof. The dimensions of the moveable handle 400 may be chosen to match those of the stationary handle 102, and may be chosen such as to provide an effective and comfortable grip for the operator. As will be described in greater detail below, the moveable handle 400 may be equipped with a slot 401 adapted to engage a moveable inner barrel (not shown in FIG. 1).

The stationary handle 102 and the moveable handle 400 are pivotally connected by lock 600. The lock 600 allows the stationary handle 102 and the moveable handle 400 to move in the same plane of motion in a scissor-like fashion. As will be shown in greater detail below, the lock 600 may be a metal screw or rivet. The lock 600 may comprise the same or different materials than the stationary handle 102 and the moveable handle 400. For example, the lock 600 may be surgical grade stainless steel or another suitable material.

The spring 900 interposes the stationary handle 102 and the moveable handle 400. The spring may be attached to the interior facing surfaces of the handles 102, 400 at a suitable location between the lock 600 and the ends of the handles 102, 400 distal from the lock 600. The spring 900 may be permanently or removably attached to the handles 102, 400. The spring 900 may be glued, screwed, or riveted in place. The spring may comprise spring steel, another type of steel, plastic, other suitable materials, and/or combinations thereof. In FIG. 1, the spring 900 is shown as two pieces in a leaf spring configuration. In other embodiments, the spring 900 may be a single piece, or may be a coil spring or other suitable implement. The spring 900 may serve to keep the device 100 in an open position when not in use. The spring 900 may also be suitably strong to force the handles 102, 400 open during use when the operator is not applying pressure to allow for easy one-handed operation of the device 100.

The outer nose 101 may be formed integrally with stationary handle 102, or they may be formed separately and then attached together, by welding or gluing, for example. The outer nose 101 may be formed of similar or different materials than the other components of the device 100. The outer nose 101 may be composed of surgical grade stainless steel, for example. The outer nose 101 may be formed by casting, machining, and/or other methods. As will be described in greater detail below, the outer nose 101 may be substantially hollow to accommodate an inner cylinder (not shown in FIG. 1).

A retaining element 500 with a knurled surface 501 may also be attached to the outer nose and/or stationary handle 102. The retaining element 500 may be composed of different or similar materials than the other components of the device 100. The retaining element may comprise surgical grade stainless steel, another metal, plastic, polymers, other suitable materials, and/or combinations thereof. The retaining element 500 may be formed by machining or casting, for example. The knurled surface may be engraved or machined into the retaining element 500.

Figure 2:
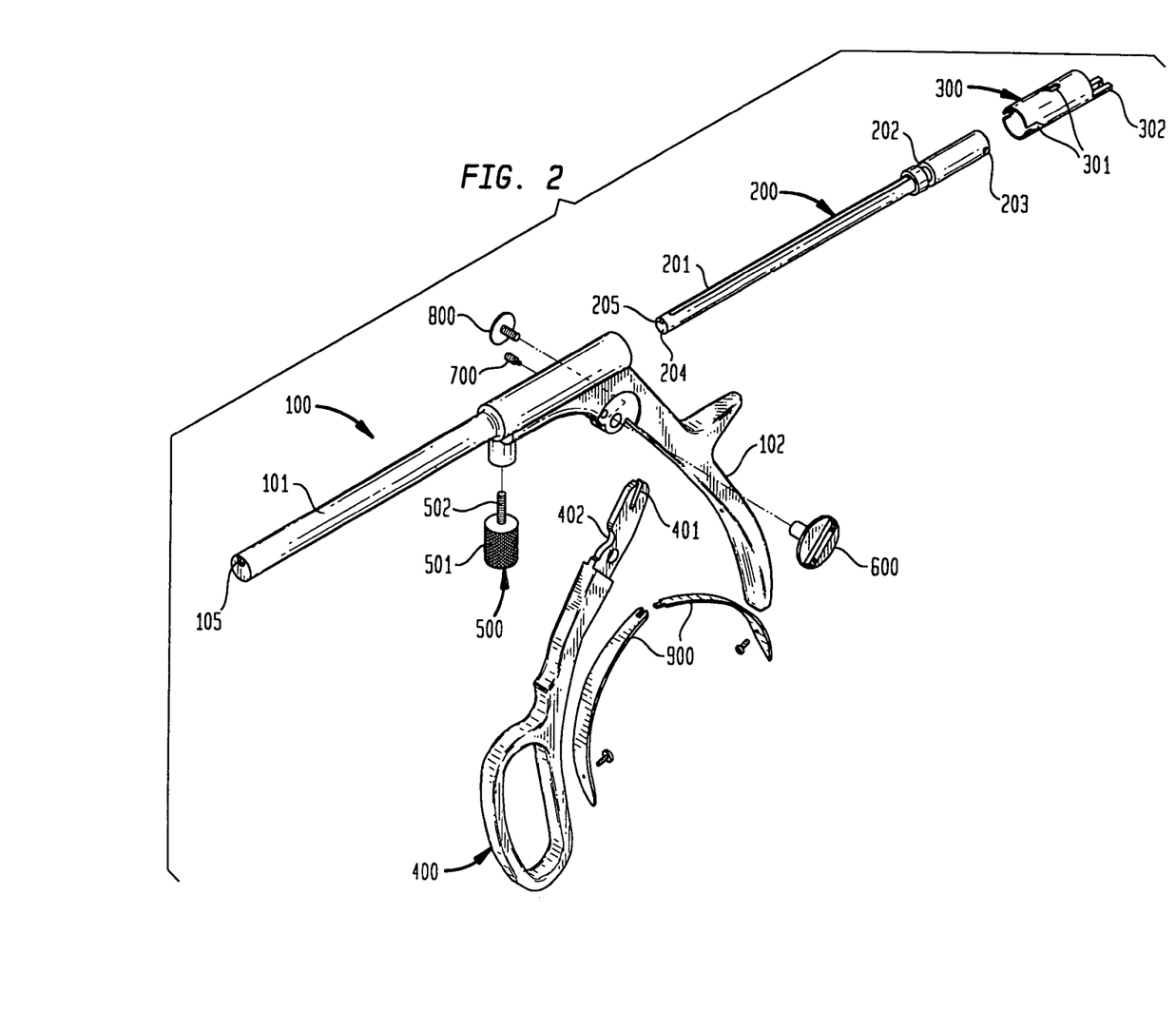
FIG. 2 is an exploded view of the device of FIG. 1.

Referring to FIG. 2, with continued reference to FIG. 1, an exploded view of one embodiment of a device 100 for cutting a surgical tension member is shown. Here it may be seen that the stationary handle 102 attaches to the moveable handle 400 pivotally by the lock 600. The lock 600 is shown here as being held in place by screws 700 and 800. The moveable handle 400 may also be seen here to have a cam surface 402 and slot 401. Also, as described previously, the spring 900, shown here as two pieces, may attach to the stationary handle 102 and moveable handle 400 by screws.

The slot 401 of the moveable handle 400 may be configured to engage a pin 302 near a first end of a movable barrel 300. The moveable barrel may be made from similar or different materials that the components previously described. In one embodiment, the barrel 300 comprises surgical grade stainless steel. The barrel 300 may be formed by casting, machining, and/or other methods. The movable barrel 300 may also have tracks or slots 301 cut or cast into it that interact with pins 203 as described below. In one embodiment, the slots 301 are arranged in a helical pattern about the walls of the barrel 300.

A cutter insert 200 may be coaxially fitted into the substantially hollow outer nose 101. In addition to pins 203, the insert 200 may also have a retaining groove 202 and a cylinder 201 with a cutting face 204 and an opening 205. The insert 200 may be hollow to allow a surgical cable to pass through to opening 205. In another embodiment, a channel may be cut lengthwise into the insert 200, which may allow a cable to pass through when the insert is inside the outer nose 101. The insert may be made from the same or different materials than the components previously described. The insert 200 may be made from surgical grade stainless steel, for example. The insert may be formed by casting, machining, or other methods. The cutting face 204 and opening 205 as well at the pins 203 may be formed integrally with the insert 200, or attached as separate components. The retaining groove 202 may be cut into the insert 200 and may be configured to engage a threaded pin 502. The threaded pin 502 may be a part of the retaining element 500 and may serve to anchor the retaining element 500 into the stationary handle 102 and retain the insert 200 in place when the device 100 is assembled. Similarly, when the device 100 is assembled, the slot 401 may engage the pin 302 to enable actuation of the device 100 as described below.

Figures 3A, 3B:
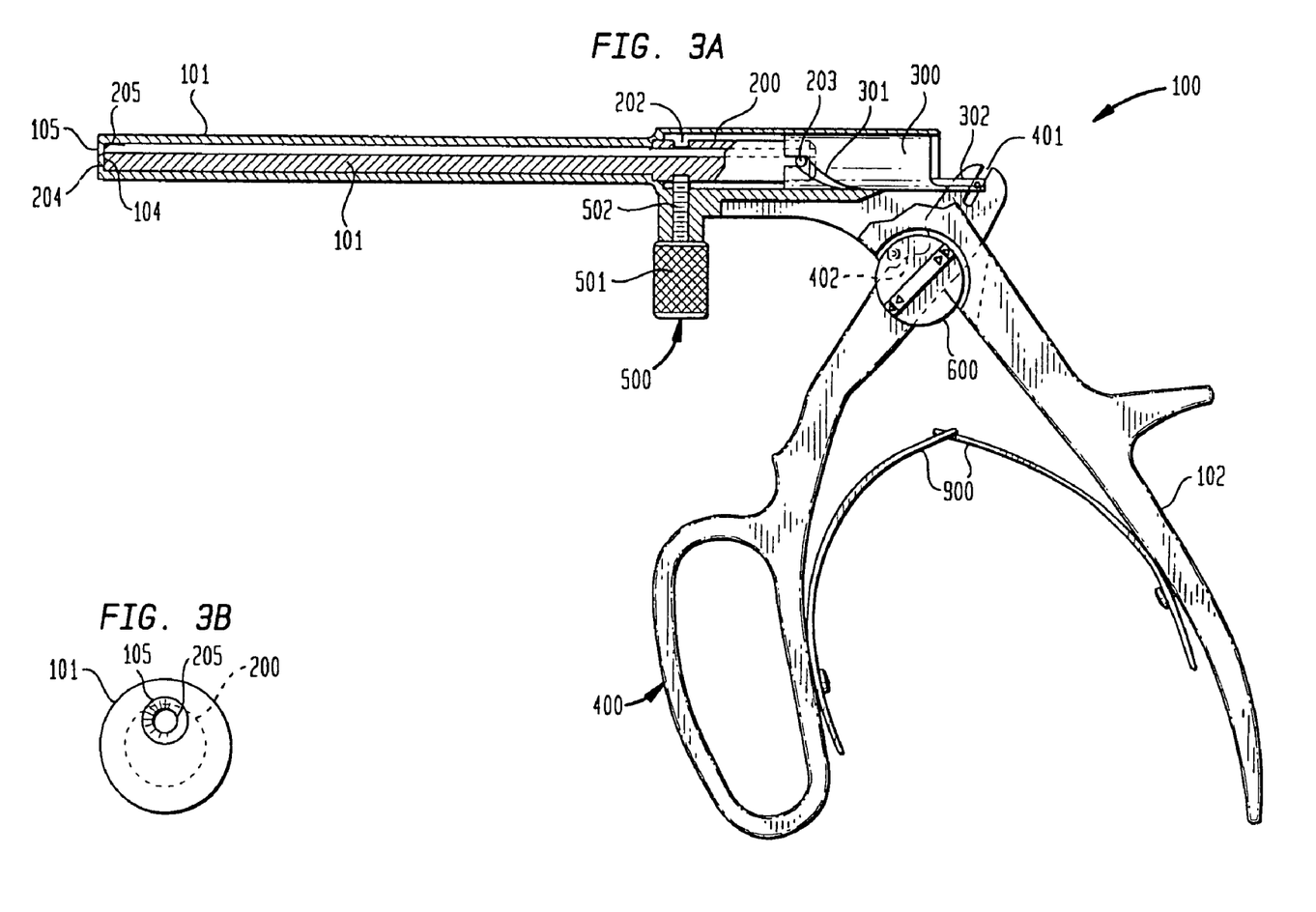
FIG. 3A is a partial cross-sectional view of the device of FIG. 1 taken along the longitudinal axis.
FIG. 3B is a partial end view of the device in FIG. 1.

Referring to FIG. 3A, with continued reference to FIGS. 1 and 2, a sectional view of one embodiment of a device 100 for cutting surgical wire or cable is shown. In FIG. 3A, the device is shown fully assembled. Here it can be seen that openings 105 and 205 align to pass a surgical tension member, such as a cable or wire. The openings are shown as circular but the device is not so limited and other shapes for the openings may be utilized. The cable or wire (not shown) may pass through the channel or hollow portion of the insert 200 and out the back of the device 100. The dimensions of the insert 200 and the outer nose 101 may be chosen such that when assembled, the cutting face 204 is substantially flush against the inside cutting surface 104 of the outer nose 101. To retain this position, the threaded pin 502 may be seen inserted into the non movable handle 102 and engaging retaining groove 202. The moveable barrel 300 may be seen engaged with pins 203 via the helical cutouts 301 and engaged with the movable handle 400 via the pin 402 and slot 401. FIG. 3A illustrates the device 100 in an "open" state to allow a wire or surgical cable to pass.

Another open view of the device 100 may be seen in FIG. 3A which is taken along the line 3B of FIG. 3A. The outer nose 101 may be seen in relation to the insert 200 (shown in broken line). Similarly, the alignment of the openings or holes 105 and 205 corresponding to the outer nose 101 and insert 200, respectively may also be seen.

Figures 4A, 4B:
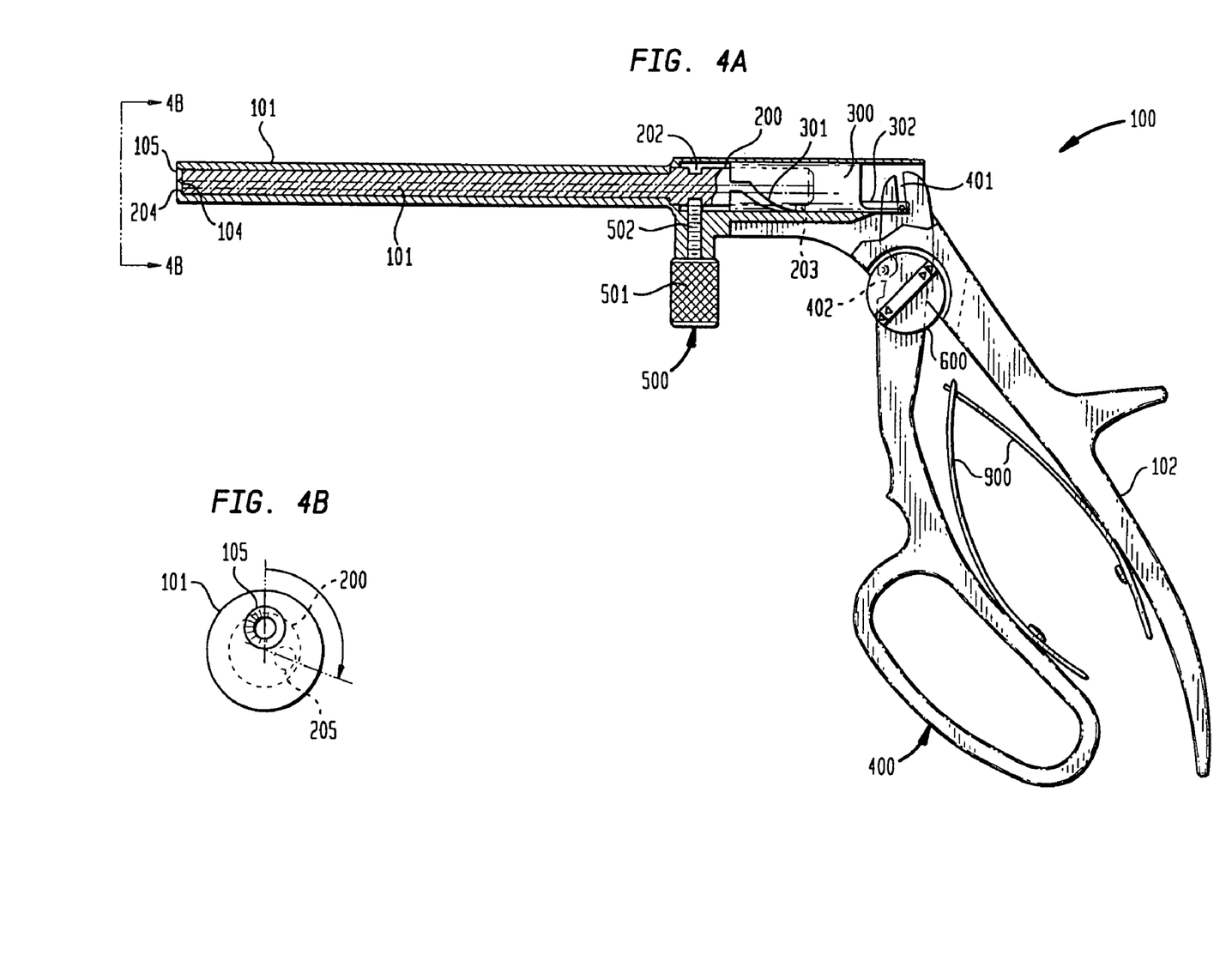
FIG. 4A is another partial cross-sectional view of the device in the cutting position.
FIG. 4B is another end view similar to FIG. 3B, showing the cutting position.

Referring to FIG. 4A, with continued reference to FIGS. 1-3, another sectional view of one embodiment of a device 100 for cutting surgical tension members is shown. Surgical tension members may include any of a variety of materials and configurations. For example the tension member may be flexible, except in the longitudinal direction, and have sufficient rigidity to hold tension such that compressive force is transmitted to adjacent tissues to resist longitudinal movement. Without limitation, examples of surgical tension members may include; cable, wire, filaments, braided strands, elongated composites, rods or other structures formed of biocompatible materials suitable for implantation.

FIG. 4A depicts the device 100 in a "closed" position. The moveable handle 400 has been drawn in toward the stationary handle 102, and the spring 900 is compressed. The movement of the movable handle 400 pivotally about the lock 600 may cause the movable handle 400 to come to rest against screw 402 when the device 100 is fully closed. Further, the slot 401 engaged with the pin 302 causes the movable barrel 300 to move along the direction of the outer nose 101. The helical slots 301 cause a rotation of the pins 203 and therefore the insert 200. The insert 200 is free to rotate in place but is prevented from moving along its axis by threaded pin 502 and retaining groove 202.

Referring now to FIG. 4B, a another view of FIG. 4A taken along the line 4B is shown. With the rotation of the insert 200 (shown in broken line) relative to the outer nose 101, the alignment of the holes 205 (shown in broken line) and 105 is also changed. Because the face 204 of the insert is flush with the interior 104 of the outer nose 101, a shearing force may cause the cable or wire inserted through the holes 105, 205 to be cut. In this way a cut in a wire or cable may be made from a direction substantially coaxial to the wire or cable. In one embodiment, the alignment of the holes 105 and 205 will become offset by about 110°, which may substantially equal the degree of rotation of the movable barrel 300. In one embodiment, this is approximately 10° beyond the intersection of the openings of the holes 105, 205. This 10° of additional travel may ensure complete cutting of the cable. Further, in one embodiment shown in FIG. 3A, the thickness between the distal surface of outer nose 101 and interior surface 104 approximates how close the cable may be sheared next to the locking element.

Figure 5:
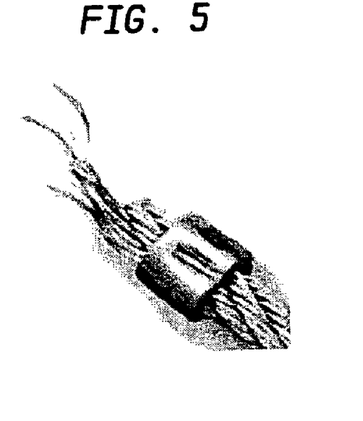
FIGS. 5-6 illustrate incomplete cuts in surgical cable.
Figure 6:
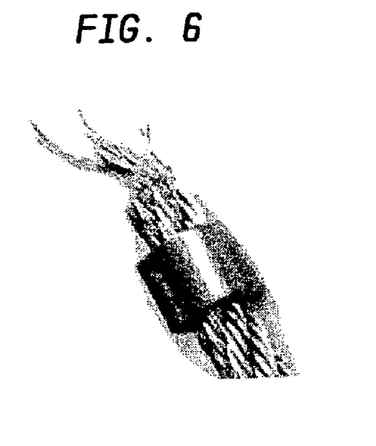
Figure 7:
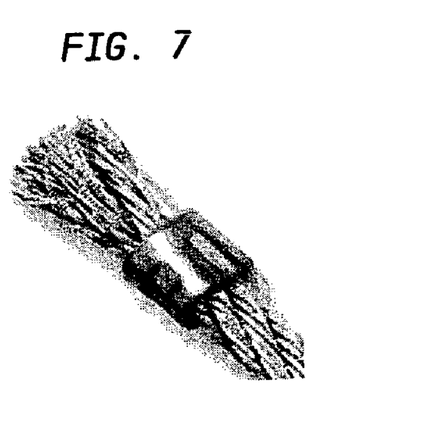
FIG. 7 illustrates a complete cut at a distance from a surgical site.
Figure 8:
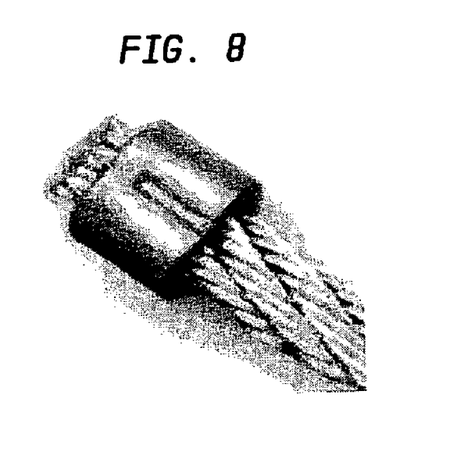
FIGS. 8-9 illustrate exemplary cuts made by the device of FIGS. 1-4.
Figure 9:
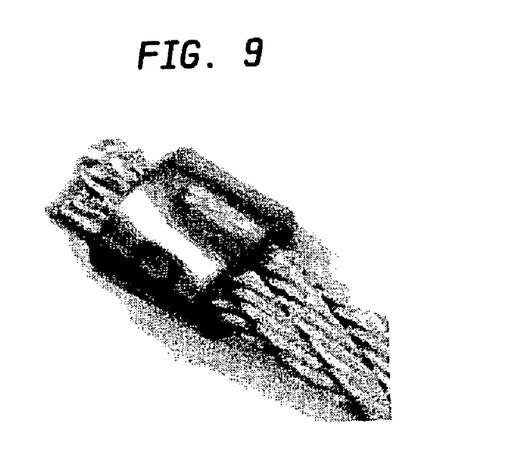

Referring now to FIGS. 5-6, incomplete cuts in surgical cables are shown. These may result, for example, from cutting of the cable with a traditional cutter at less than an optimal angle (e.g., within a surgical cavity). FIG. 7 illustrates a complete cut at a distance from a surgical site, which may also result, for example, due to difficulties with placing traditional cutting device in an optimal position within the surgical cavity. FIGS. 8-9 illustrate exemplary cuts, which may be made by the device 100 of FIGS. 1-4, even within a surgical cavity.

Figure 10A:
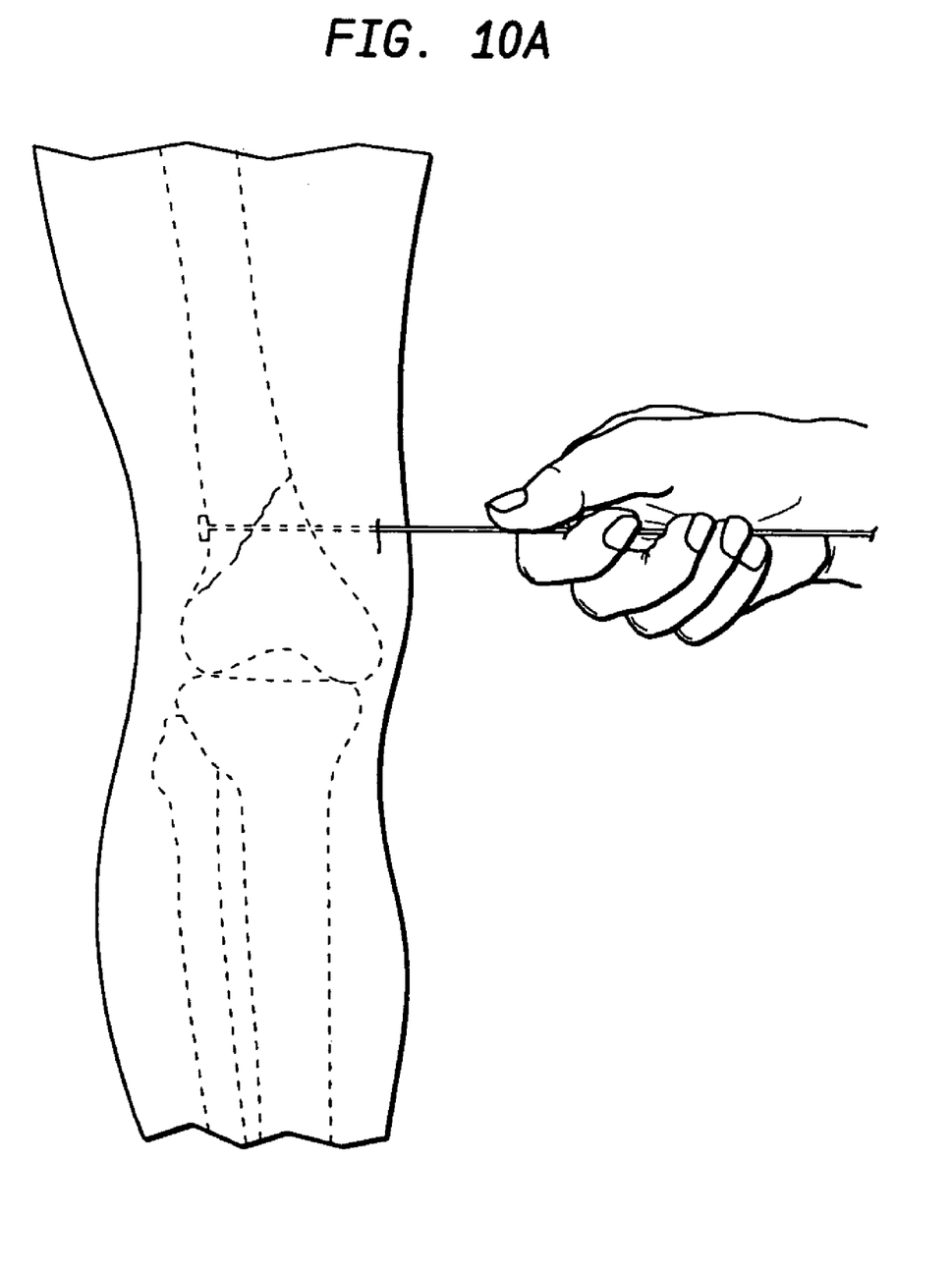
FIG. 10A illustrates one possible surgical procedure utilizing aspects of the present disclosure.
Figure 10B:
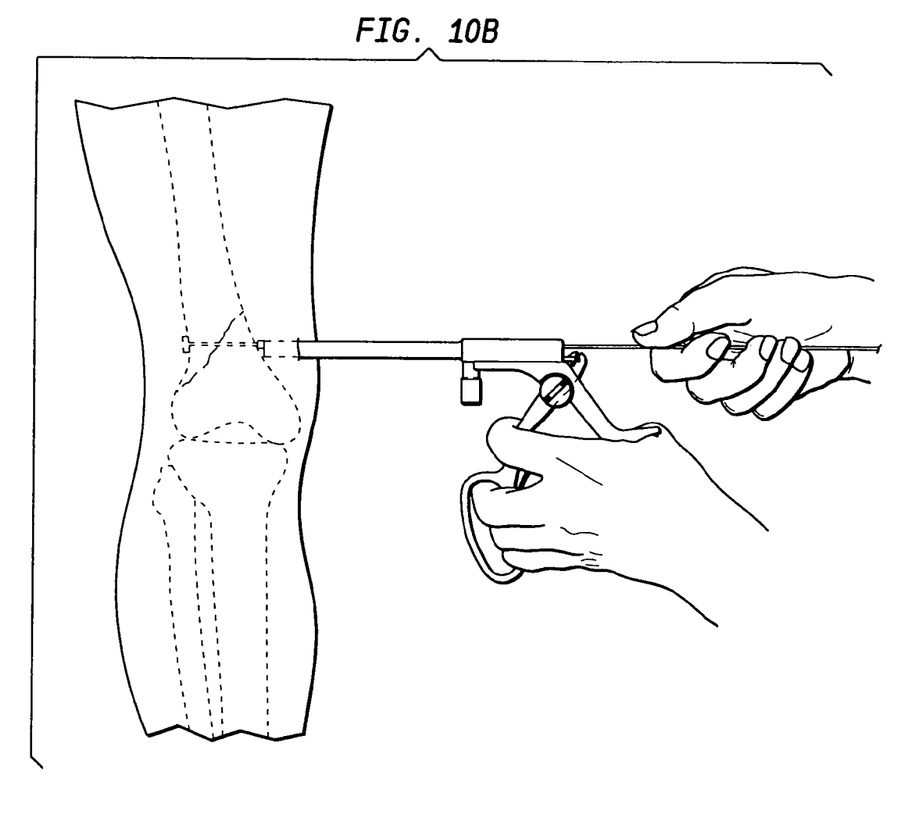
FIG. 10B shows one step in the surgical procedure of FIG. 10A utilizing the device of FIGS. 1-4.

Referring to FIG. 10A, with continued reference to FIGS. 1-9, one possible surgical procedure utilizing aspects of the present disclosure is illustrated. A surgical site is shown here in which a cable or wire has been used to close a fracture. Referring to FIG. 10B, with continued reference FIGS. 1-10A, the device 100 is shown in operation. After the cable or wire implant has been inserted, it may be tensioned and affixed to a locking element such as the crimps shown in FIGS. 5-9. Following crimping, it may be necessary to trim off the excess cable that was required for anatomical reduction and instrumentation. The device of FIGS. 1-4 may be utilized to provide a reproducible cut as close to the surgical crimp as possible. The device may be inserted into the same incision as was used to access the surgical site and for the crimping and tensioning. The device may be passed over the length of cable, advanced through the soft tissue incision, down to the site of the crimp until the instrument stops upon contact with the crimp. In one aspect the outer nose has a length sufficient to position the handles outside the patient. Slight tension may be applied to the cable extending from the back of the device to ensure that the cutter is fully seated against the surgical crimp. With the opposite hand, the handles of the device may be actuated (while still maintaining slight tension on the free cable). Once the cable has been successfully cut, the free cable abruptly releases from the surgical site and the cut cable is discarded. The operator may wish to take one ore more radiographs at varying perspectives to ensure that tension has not been lost and reduction and fixation of the fracture was successful.

Those skilled in the art should appreciate that they may readily use the present disclosure as a basis for designing or modifying other processes and structures for carrying out the same purposes and/or achieving the same advantages of the embodiments introduced herein. For example, various steps of the described methods and sequences may be executed in a different order or executed sequentially, combined, further divided, replaced with alternate steps, or removed entirely. In addition, various functions illustrated in the methods or described elsewhere in the disclosure may be combined to provide additional and/or alternate functions. Those skilled in the art should also realize that such equivalent constructions do not depart from the spirit and scope of the present disclosure, and that they may make various changes, substitutions, and alterations herein without departing from the spirit and scope of the present disclosure.

The present inventions may find application in many medical procedures. For example, but without limitation, such surgical procedures can include those disclosed in U.S. Pat. Nos. 6,019,762 and 6,068,648 to Cole et al., incorporated herein by reference in their entirety.

What is claimed is:

1. A method of cutting a surgical tension member comprising:
   setting a fractured bone in a desired position utilizing a length of a surgical tension member;
   crimping a locking element to the surgical tension member next to the bone utilizing a surgical opening;
   inserting a proximal end of the surgical tension member into a distal end of a surgical device, the surgical device having outer and inner tubular coaxial members with coordinating, off-center, substantially circular openings on the distal end, the substantially circular openings being substantially aligned with one another when the proximal end of the surgical tension member is inserted, the substantially circular openings receiving the proximal end of the surgical tension member;
   moving the distal end of the outer and inner coaxial members along the surgical tension member and into the surgical opening to contact the locking element without allowing the locking element to pass into the substantially circular opening of the outer tubular coaxial member;
   applying tension to a portion of the surgical tension member extending out of a proximal portion of the surgical device to urge the distal end of the surgical device against the locking element;
   while applying tension to the portion of the surgical tension member, actuating handles of the surgical device to cause rotation of the coaxial members with respect to one another to move the substantially circular openings with respect to one another such that curved edges of the circular openings exert a shear cutting force on the surgical tension member to sever a length thereof, wherein a threaded pin of a retaining element allows rotation of the inner coaxial member relative to the outer coaxial member while limiting translation of the inner coaxial member relative to the outer coaxial member during actuation of the handles; and
   removing the severed length of the surgical tension member and the surgical device from the surgical opening.

2. The method according to claim 1 further comprising performing all steps within the same surgical cavity.

3. The method according to claim 1 wherein the tension member is inserted through the cutting surgical device via the substantially aligned off-center circular openings in the coaxial members.

4. The method of claim 1 actuating the handles of the surgical device comprises compressing a compressible handle.

5. The method of claim 1 wherein the coaxial members are rotated through about 110° relative to one another.

6. The method of claim 5, wherein the off-center circular openings of the coaxial members are substantially aligned prior to rotation of the coaxial members and wherein the off-center circular openings of the coaxial members do not intersect after about 110° rotation of the coaxial members relative to one another.

7. The method of claim 6, wherein the about 110° rotation of the coaxial members relative to one another causes the off-center circular openings to rotate approximately 10° beyond an intersection of the off-center circular openings of the coaxial members.

8. The method of claim 1, wherein rotating the coaxial members with respect to one another comprises rotating the inner coaxial member while maintaining the position of the outer coaxial member.

9. The method of claim 1, wherein when the locking element contacts the distal end of the outer coaxial member without passing into the substantially circular opening of the outer coaxial member, the locking element is spaced from the inner coaxial member.

10. The method of claim 9, wherein rotating the coaxial members comprises rotating the coaxial members to a position where the off-center circular openings do not overlap one another.

11. A method of cutting a surgical tension member comprising:
    setting a fractured bone in a desired position utilizing a length of a surgical tension member;
    tensioning and affixing a locking element to the surgical tension member next to the bone through a surgical opening;
    inserting a proximal end of the surgical tension member into and in-line with a longitudinal member of a cutting surgical device, the longitudinal member having an outer, tubular coaxial member and an inner, tubular coaxial member, the inner and outer coaxial members having coordinating, off-center, circular openings on a distal end, and wherein the inner coaxial member is substantially disposed within the outer coaxial member, the inner coaxial member further having at least one pin radially attached on a circumference of a proximal end;
    moving the distal end of the longitudinal member along the surgical tension member and into the surgical opening to contact the locking element on an exterior surface of the outer tubular member distal end; and
    rotating the inner and outer coaxial members with respect to one another to exert a shear cutting force on the surgical tension member to sever a length thereof, wherein the rotation of the coaxial members is achieved by depressing a handle, the handle being operably connected to a movable barrel, the movable barrel interposing the inner and outer coaxial members along a length of a portion of the proximal ends of each and having at least one helical groove configured to engage the at least one pin of the inner coaxial member;
    wherein the inner coaxial member includes an annular retaining groove that receives a locking pin inserted through a proximal portion of the outer coaxial member, the engagement between the locking pin and the annular retaining groove preventing translation of the inner coaxial member relative to the outer coaxial member;

wherein affixing the locking element to the surgical tension member comprises crimping the locking element to the surgical tension member.

12. The method of claim 11, wherein the off-center circular openings of the coaxial members are substantially aligned when the proximal end of the surgical tension member is inserted, and wherein rotating the inner and outer coaxial members comprises rotating the coaxial members such that the off-center circular openings do not overlap one another.

13. The method of claim 12, wherein the surgical tension member is inserted into the off-center circular openings.

* * * * *